US00PP18137P2

(12) United States Plant Patent
Kievit

(10) Patent No.: US PP18,137 P2
(45) Date of Patent: Oct. 23, 2007

(54) ***NEMESIA* PLANT NAMED 'KIENEBLU'**

(50) Latin Name: *Nemesia caerulea*
Varietal Denomination: Kieneblu

(75) Inventor: Christa Kievit, Hem (NL)

(73) Assignee: Kieft Bloemzaden B.V., Venhuizen (NL)

( * ) Notice: Subject to any disclaimer, the term of this patent is extended or adjusted under 35 U.S.C. 154(b) by 0 days.

(21) Appl. No.: 11/444,237

(22) Filed: May 31, 2006

(51) Int. Cl.
*A01H 5/00* (2006.01)

(52) U.S. Cl. ..... Plt./263
(58) Field of Classification Search ..... Plt./263
See application file for complete search history.

*Primary Examiner*—Kent Bell
*Assistant Examiner*—June Hwu
(74) *Attorney, Agent, or Firm*—C. A. Whealy

(57) ABSTRACT

A new and distinct cultivar of *Nemesia* plant named 'Kieneblu', characterized by its upright and outwardly spreading growth habit; freely branching and flowering plant habit; and dark violet-colored flowers.

1 Drawing Sheet

Botanical designation: *Nemesia caerulea.*
Cultivar denomination: 'Kieneblu'.

BACKGROUND OF THE INVENTION

The present invention relates to a new and distinct cultivar of *Nemesia,* botanically known as *Nemesia caerulea* and hereinafter referred to by the name 'Kieneblu'.

The new *Nemesia* is a product of a planned breeding program conducted by the Inventor in Venhuizen, The Netherlands. The objective of the breeding program is to create new outwardly spreading *Nemesia* cultivars with attractive foliage shape and coloration.

The new *Nemesia* originated from a cross-pollination made by the Inventor during the spring of 2001 in Venhuizen, The Netherlands of a proprietary selection of *Nemesia caerulea* identified as code number HW 295-1, not patented, as the female, or seed, parent with a proprietary selection of *Nemesia caerulea* identified as code number HW 225, not patented, as the male, or pollen, parent. The new *Nemesia* was discovered and selected by the Inventor as a single flowering plant within the progeny of the stated cross-pollination in a controlled environment in Venhuizen, The Netherlands during the summer of 2002.

Asexual reproduction of the new *Nemesia* by terminal cuttings in a controlled environment in Venhuizen, The Netherlands since 2002, has shown that the unique features of this new *Nemesia* are stable and reproduced true to type in successive generations.

SUMMARY OF THE INVENTION

The cultivar Kieneblu has not been observed under all possible environmental conditions. The phenotype may vary somewhat with variations in environment and cultural practices such as temperature, daylength and light intensity without, however, any variance in genotype.

The following traits have been repeatedly observed and are determined to be the unique characteristics of 'Kieneblu'. These characteristics in combination distinguish 'Kieneblu' as a new and distinct cultivar of *Nemesia:*

1. Upright and outwardly spreading growth habit.
2. Freely branching and flowering plant habit.
3. Dark violet-colored flowers.

Compared to plants of the parent selections, plants of the new *Nemesia* are more uniform and more outwardly spreading.

Plants of the new *Nemesia* can also be compared to plants of the cultivar Sumnem 03, disclosed in U.S. Plant Pat. No. 16,527. In side-by-side comparisons conducted in Venhuizen, The Netherlands, plants of the new *Nemesia* and the cultivar Sumnem 03 differed primarily in flower color as plants of the cultivar Sumnem 03 had lighter purple-colored flowers.

BRIEF DESCRIPTION OF THE PHOTOGRAPHS

The accompanying colored photographs illustrate the overall appearance of the new *Nemesia,* showing the colors as true as it is reasonably possible to obtain in colored reproductions of this type. Colors in the photographs may differ slightly from the color values cited in the detailed botanical description which accurately describe the colors of the new *Nemesia.*

The photograph at the bottom of the sheet comprises a side perspective view of a typical flowering plant of 'Kieneblu' grown in a container.

The photograph at the top of the sheet comprises a close-up of typical flowers of 'Kieneblu'.

DETAILED BOTANICAL DESCRIPTION

The photographs and following observations, measurements and values describe plants grown in Lompoc, Calif., under commercial practice during the winter in a polycarbonate-covered greenhouse with day temperatures ranging from 21° C. to 24° C., night temperatures ranging from 16° C. to 18° C., and light levels ranging from about 4,000 to 8,000 foot candles. Plants were grown for about 18 weeks with one plant per 12.5-cm container. In the following description, color references are made to The Royal Horticultural Society Colour Chart, 1995 Edition, except where general terms of ordinary dictionary significance are used.

Botanical classification: *Nemesia caerulea* cultivar Kieneblu.

Parentage:

*Female, or seed, parent.*—Proprietary selection of *Nemesia caerulea* identified as code number HW 295-1, not patented.

*Male, or pollen, parent.*—Proprietary selection of *Nemesia caerulea* identified as code number HW 225, not patented.

Propagation:

*Type.*—By terminal cuttings.

*Time to produce a rooted young plant.*—About two weeks at temperatures of 21° C.

*Root description.*—Fine; white in color.

*Rooting habit.*—Freely branching; dense.

Plant description:

*Plant and growth habit.*—Upright and outwardly spreading; loose open plant form. Freely branching; about four primary branches per plant and numerous secondary branches. Moderate growth habit.

*Plant height.*—About 21 cm.

*Plant diameter.*—About 29 cm by 33 cm.

Lateral branch description:

*Length.*—About 30 cm.

*Diameter.*—About 3 mm.

*Internode length.*—About 1.8 cm.

*Strength.*—Strong.

*Aspect.*—Initially upright to outwardly spreading.

*Texture.*—Smooth, glabrous.

*Color.*—144A.

Foliage description:

*Arrangement.*—Opposite, simple; sessile.

*Length.*—About 3.2 cm.

*Width.*—About 2 cm.

*Shape.*—Elliptic to somewhat deltoid.

*Apex.*—Broadly acute.

*Base.*—Attenuate; clasping.

*Margin.*—Serrate.

*Texture, upper and lower surfaces.*—Smooth, glabrous.

*Venation pattern.*—Pinnate; arcuate.

*Color.*—Developing foliage, upper surface: 146A. Developing foliage, lower surface: 147B. Fully expanded foliage, upper surface: 147A; venation, 147A. Fully expanded foliage, lower surface: 147B; venation, 147C.

Flower description:

*Flower arrangement and habit.*—Zygomorphic solitary flowers arranged on terminal racemes; flowering acropetally towards the apex. Flowers bilabiate with nectar spur. Flowers face upright and outwardly. Flowers last about four to five days on the plant. Flowers not persistent. Freely flowering habit with about 22 to 26 open flowers and flower buds developing per raceme.

*Fragrance.*—None detected.

*Natural flowering season.*—In northern Europe, plants flower from early spring to fall; flowering continuous during this period.

*Inflorescence height.*—About 6 cm to 7 cm.

*Inflorescence diameter.*—About 3.5 cm.

*Flower length.*—About 2 cm.

*Flower width.*—About 2 cm.

*Flower depth.*—About 1.7 cm.

*Flower buds.*—Shape: Oval with spur. Length, including spur: About 7 mm. Diameter: About 5 mm. Color: 77C.

*Petals.*—Arrangement: Five petals; four upper petals are fused at base to form an upright lobed and arched banner lip; lower petal modified into a larger lip with nectar spur and convex oval protuberance which serves as a pollinator nectar guide and landing platform. Shape: Oval to obovate. Apex: Rounded. Margin: Entire. Length: Upper petals: About 1 cm. Lateral petals: About 8 mm. Lower petal: About 1.1 cm. Width: Upper petals: About 5 mm. Lateral petals: About 6 mm. Lower petal: About 1.2 cm. Nectar spur length: About 6 mm. Nectar spur diameter: About 1 mm. Texture, upper and lower surfaces: Smooth, glabrous. Color: When opening, upper surface: 83C. When opening, lower surface: 76A. Fully opened, upper surface: 86D; color becoming closer to slightly more grey than 86D with development. Fully opened, lower surface: 76A. Nectar guide: 12A; at base, 155D. Nectar spur: 145D.

*Sepals.*—Arrangement: Calyx star-shaped with five sepals fused at the base. Shape: Elliptic to lanceolate. Apex: Acute. Margin: Entire. Length: About 3 mm. Width: About 1 mm. Texture, upper and lower surfaces: Pubescent; minute. Color: Immature, upper and lower surfaces: 146A. Mature, upper surface: 147A. Mature, lower surface: 147B.

*Peduncles.*—Length: About 4.5 cm. Diameter: About 2 mm. Angle: About 45° from vertical. Strength: Strong. Texture: Pubescent; sparse. Color: 146B.

*Pedicels.*—Length: About 7 mm. Diameter: About 1 mm. Angle: About 45° to 60° from peduncle axis. Strength: Strong. Texture: Pubescent; minute. Color: 144B.

*Reproductive organs.*—Stamens: Quantity/arrangement: Four per flower. Anther shape: Oval. Anther length: Less than 1 mm. Anther color: 10A. Pollen amount: Scarce. Pollen color: 10A. Pistils: Quantity: One per flower. Pistil length: About 2 mm. Style length: About 1 mm. Style color: 145D. Stigma shape: Rounded. Stigma color: 145C. Ovary color: 145A. Seed/fruit: Seed and fruit development have not been observed on plants of the new *Nemesia*.

Temperature tolerance: Plants of the new *Nemesia* have been observed to tolerate temperatures from about 10° C. to about 35° C.

Pathogen/pest resistance: Plants of the new *Nemesia* have not been observed to be resistant to pests and pathogens common to *Nemesia*.

It is claimed:

1. A new and distinct *Nemesia* plant named 'Kieneblu' as illustrated and described.

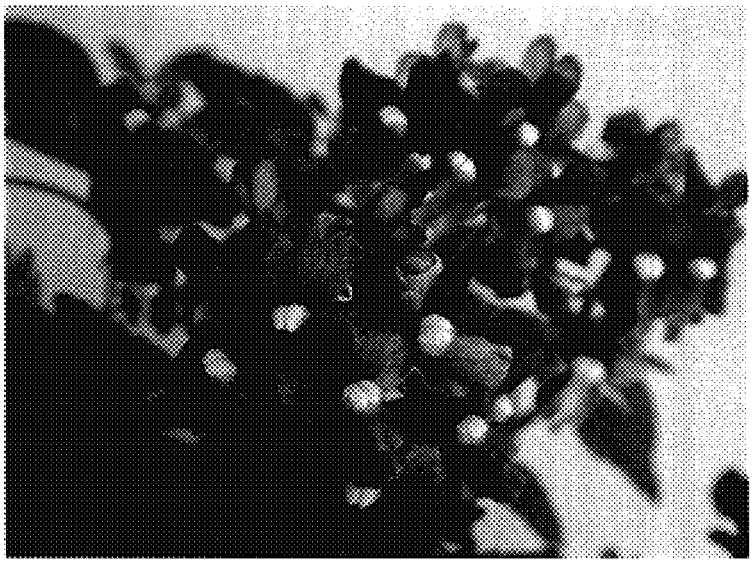
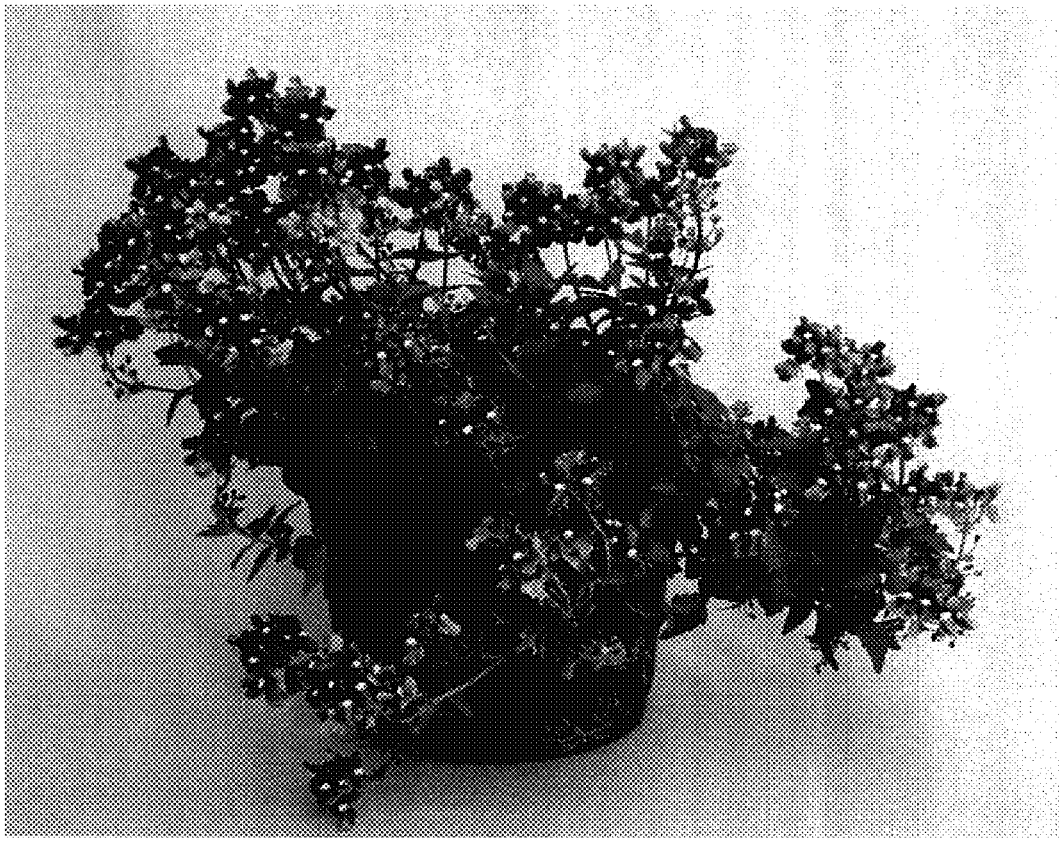

* * * * *